(12) United States Patent
Swaile et al.

(10) Patent No.: US 8,883,129 B2
(45) Date of Patent: Nov. 11, 2014

(54) ENHANCED EFFICACY ANTIPERSPIRANT ACTIVE

(75) Inventors: David Frederick Swaile, Cincinnati, OH (US); Wayne Edward Beimesch, Crestview Hills, KY (US); David Good, Loveland, OH (US); Scott Edward Smith, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 1973 days.

(21) Appl. No.: 11/034,477

(22) Filed: Jan. 13, 2005

(65) Prior Publication Data

US 2006/0153788 A1 Jul. 13, 2006

(51) Int. Cl.
*A61K 8/00* (2006.01)
*A61Q 15/00* (2006.01)
*A61K 8/26* (2006.01)

(52) U.S. Cl.
CPC .. *A61Q 15/00* (2013.01); *A61K 8/26* (2013.01)
USPC ........................................... 424/65

(58) Field of Classification Search
None
See application file for complete search history.

(56) References Cited

U.S. PATENT DOCUMENTS

| | | | |
|---|---|---|---|
| 2,571,030 A | 10/1951 | Govett et al. | |
| 3,509,253 A | 8/1970 | Babbin | |
| 3,876,758 A | 4/1975 | Beekman | |
| 3,904,741 A | 9/1975 | Jones et al. | |
| 4,108,977 A | 8/1978 | Kenkare et al. | |
| 4,359,456 A | 11/1982 | Gosling et al. | |
| 4,818,512 A | 4/1989 | Markarian et al. | |
| 4,859,446 A | 8/1989 | Abrutyn et al. | |
| 4,944,933 A | 7/1990 | Inward | |
| 5,114,705 A | 5/1992 | Callaghan et al. | |
| 5,234,677 A | 8/1993 | Murray et al. | |
| 5,298,640 A * | 3/1994 | Callaghan et al. | 556/27 |
| 5,358,694 A * | 10/1994 | Giovanniello | 423/462 |
| 5,589,196 A | 12/1996 | Callaghan et al. | |
| 5,718,876 A * | 2/1998 | Parekh et al. | 423/462 |
| 5,770,186 A | 6/1998 | Callaghan et al. | |
| 6,042,816 A | 3/2000 | Shen | |
| 6,342,210 B1 * | 1/2002 | Cai et al. | 424/65 |
| 2004/0091436 A1 | 5/2004 | Li et al. | |

FOREIGN PATENT DOCUMENTS

| | | |
|---|---|---|
| EP | 0256832 B1 | 4/1992 |
| EP | 0191628 B1 | 11/1993 |
| WO | WO 00/71091 A1 | 11/2000 |
| WO | WO 2004/052325 A1 | 6/2004 |

* cited by examiner

*Primary Examiner* — Snigdha Maewall
(74) *Attorney, Agent, or Firm* — Betty J. Zea; Andrew J. Hagerty

(57) ABSTRACT

An enhanced efficacy aluminum only salt active. The method for making such active comprises the steps of (a) providing an aqueous solution of an aluminum salt having a Band III polymer concentration of at least about 20%; (b) adding to the aqueous solution of step (a) an aqueous solution of a monomeric aluminum salt to form a mixture; and (c) rapidly drying the mixture to form a product powder. The active comprises an aluminum only salt having a Band III polymer concentration of at least about 20%, an aluminum to anion ratio of from about 1.1:1 to about 1.8:1 and a level of monomeric aluminum of from about 2% to about 20% of the total aluminum.

11 Claims, 1 Drawing Sheet

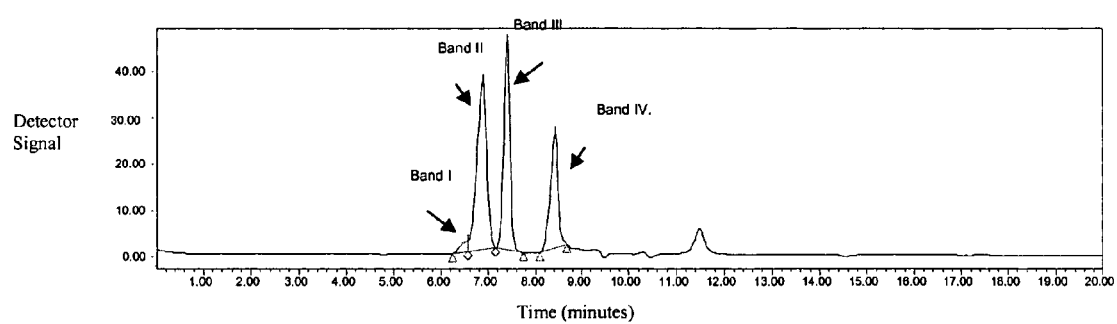

ENHANCED EFFICACY ANTIPERSPIRANT ACTIVE

FIELD OF THE INVENTION

The present invention relates to antiperspirant products, specifically, an enhanced efficacy aluminum-only active and the process for making the same.

BACKGROUND OF THE INVENTION

There are many types of topical antiperspirant products that are commercially available or otherwise known in the antiperspirant art. These products typically contain an antiperspirant active in the form of an aluminum and/or zirconium salt and which are formed by the partial neutralization of acidic aluminum ($Al^{+3}$) and zirconium ($Zr^{+4}$) metal ions. The partial neutralization results in the formation of aluminum and zirconium hydrolysis polymers of complex structure. Without being bound by theory, it is believed that these actives reduce perspiration flow to the skin surface by forming shallow blockages within the sweat ducts that carry the perspiration to the skin surface.

Aluminum-only salts may include aluminum chloride and basic aluminum salts such as aluminum chlorohydrate, aluminum sesquichlorohydrate and aluminum dichlorohydrate. Often, these aluminum salts are mixed with zirconium salts (e.g., zirconium hydroxy chloride) to make combination salts such as aluminum zirconium trichlorohydrate and aluminum zirconium tetrachlorohydrate. Aluminum zirconium salts are generally believed to be more efficacious than aluminum-only salts due to the more acidic nature of zirconium salts in the mixture. Without being bound by theory, the increased acidity is believed to increase the lifetime of the blockage that provides the reduction in perspiration flow.

To improve the efficacy of aluminum-only actives such as aluminum chlorohydrates, one can control the process of making the actives in order to provide a higher concentration of lower molecular weight hydrolysis polymers. It is generally accepted that actives with higher concentrations of Band III polymers, as measured by gel permeation chromatography, have higher efficacy. Thus, there are many methods known in the art to increase the level of Band III polymers including heating or aging actives. When aluminum salts possessing a high level of Band III polymers are used to produce aluminum zirconium salts, an efficacy increase occurs thereby providing actives that are typically more efficacious than aluminum-only actives having similar levels of Band III polymers.

While aluminum zirconium salts are desirable as an antiperspirant active, the increasing costs of zirconium raw materials may impede or prohibit the use of such materials in products. Moreover, zirconium salts are prohibited for use in aerosol products, which are the preferred product form in some markets. Thus, there is a need to improve the efficacy of aluminum-only salts such that they are equal to or exceed the efficacy of aluminum zirconium salts with high levels of band III polymer.

Accordingly, the present invention provides an enhanced efficacy antiperspirant active using an improved aluminum-only salt and a process for making the active. Particularly, the present invention provides an enhanced efficacy antiperspirant active comprising an improved aluminum-only salt having a Band III level polymer of at least about 20% and comprising a level of monomeric aluminum ranging from about 2% to about 20% of the total aluminum wherein the aluminum to anion ratio is from about 1.1:1 to about 1.8:1. Furthermore, the present invention provides a process for making an enhanced efficacy aluminum-only salt active by providing a solution of an aluminum hydroxyhalide salt having at least about 20% of a Band III polymer, mixing with a solution of a monomeric aluminum salt and rapidly drying the mixture to form a product powder.

SUMMARY OF THE INVENTION

The present invention relates to an enhanced efficacy antiperspirant active comprising an aluminum-only salt having a Band III polymer concentration of at least about 20%, an aluminum to anion ratio of from about 1.1:1 to about 1.8:1 and a level of monomeric aluminum of from about 2% to about 20% of the total aluminum.

The present invention also relates to a method for making an enhanced efficacy aluminum-only salt active, said method comprising the steps of: (a) providing an aqueous solution of an aluminum salt having a Band III polymer of at least about 20%, (b) adding an aqueous solution of a monomeric aluminum salt to said aqueous solution of step (a) to form a mixture and (c) rapidly drying the mixture to form a product.

BRIEF DESCRIPTION OF THE DRAWINGS

FIG. 1 is a chromatogram of Bands I, II, II and IV of the aluminum-only salts of the present invention.

DETAILED DESCRIPTION OF THE INVENTION

While the specification concludes with the claims particularly pointing and distinctly claiming the invention, it is believed that the present invention will be better understood from the following description.

As used herein, "comprising" means that other steps and ingredients can be added. This term encompasses the terms "consisting of" and "consisting essentially of". The phrase "consisting essentially of" means that the composition may include additional ingredients or the process may include additional steps, but only if the additions do not materially alter the basic and novel characteristics of the claimed compositions or methods.

All percentages, parts and ratios are based upon the total weight of the topical compositions of the present invention and all measurements made are at 25° C., unless otherwise specified. All such weights as they pertain to listed ingredients are based on the active level and, therefore, do not include carriers or by-products that may be included in commercially available materials, unless otherwise specified.

As used herein, the term "aluminum-only salt" refers to antiperspirant salts that are substantially free of zirconium.

Process

The process of the present invention comprises the mixing of an aqueous solution of aluminum hydroxyhalide salt having a Band III polymer concentration of at least about 20% with an aqueous solution of a monomeric aluminum salt and then rapidly drying the mixture to form a powder suitable for topical application to the skin as an antiperspirant active in an antiperspirant product.

The aqueous solution of the aluminum hydroxyhalide salts used in the present invention have a Band III polymer concentration of at least about 20%. The aqueous solution of the aluminum hydroxyhalide salts used in this process may also have, for example, a Band III polymer concentration of at least about 25% or at least about 30% as measured by the method described below. The concentration of the Band III polymer can be achieved by any method know in the art.

Methods which can be used to increase Band III polymers in the aqueous solution of the aluminum hydroxyhalide salt include any method that is capable of providing a certain total aluminum salt concentration in the aqueous solution of the aluminum hydroxyhalide salt. For example, the total aluminum salt concentration may be at least about 10%, at least about 15% or at least about 20%.

The aluminum salt includes inorganic and organic salts of aluminum as well as mixtures of such salts. For example, the salts of the present invention may be salts or salts derived from aluminum halides, aluminum hydroxyhalides, aluminum chlorohydrates and mixtures thereof, and include aluminum salts which conform to the formula:

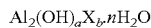

$$Al_2(OH)_aX_b \cdot nH_2O$$

wherein a is from about 0 to about 5; the sum of a and b is about 6; n is from about 1 to about 6; and wherein a, b, and n may have non-integer values. X may be any anion capable of providing a counter ion to the aluminum ion. For example, X may be a halogen ion including chloride, fluoride, bromide or iodide. Further, for example, salts of the present invention may be aluminum hydroxyhalides that comprise a chloride ion and which are referred to as aluminum chlorohydroxides. For example, the aluminum chlorohydroxides may be referred to as 5/6 basic chlorohydroxide or aluminum chlorohydrate, wherein a is about 5 and having a metal to chloride molar ratio of about 1.9 to about 2.1; or 2/3 basic chlorohydroxide or aluminum sequichlorohydrate, wherein a is about 4 and having a metal to chloride molar ratio of about 1.25 to about 1.9.

The aluminum hydroxyhalide salts may be prepared by any method known or otherwise effective in making such aluminum salts as antiperspirant active materials. For example, the present invention may use aluminum chlorohydroxide salts with aluminum to chloride molar ratios greater than about 1.5:1. Also, for example, the present invention may use aluminum chlorohydroxide salts with aluminum to chloride molar ratios greater than about 1.8:1. These ratios allow the addition of the desired levels of aluminum chloride without reducing the aluminum to chloride molar ratio below about 1.1 to about 1 of the desired active.

Monomeric aluminum salts of the present invention may comprise any anion capable of providing a counter ion to the aluminum ion. For example, the anion may be a halogen ion including chloride, fluoride, bromide or iodide. While the monomeric aluminum salt solutions of the present invention may fluctuate, the solutions may comprise an aluminum to anion molar concentration of, for example, from about 0.1:1 to about 1:1 or from about 0.3:1 to about 0.4:1. The concentration of the monomeric aluminum salt is dependent on the concentration of the aqueous solution of the aluminum hydroxyhalide salt to which it will be added. The concentration of the monomeric aluminum salt is also dependent on the mixing equipment and desired aluminum to anion molar ratio of the final active. Higher concentrations of monomeric aluminum salt help to reduce the amount of water that must be removed during drying. The monomeric aluminum salt solution may be heated but it is usually processed at ambient temperatures.

The ratio of the aqueous solution of the aluminum hydroxyhalide salts having a Band III polymer concentration of at least about 20% to the aqueous solution of monomeric aluminum salt will depend on the aluminum to anion ratio of the aluminum hydroxyhalide salt, the aluminum to anion ratio of the monomeric aluminum salt solution, the desired aluminum to anion ratio of the final product, the desired level of monomeric aluminum salt and the consideration that there may be potential for anion loss during drying. One skilled in the art will be able to adjust these variables in order to achieve the desired aluminum-only salt of the present invention. For example, ratios of the aqueous solution of the aluminum hydroxyhalide salts having a Band III polymer concentration of at least about 20% to the aqueous solution of monomeric aluminum salt may be from about 1:1.5 to about 1:0.05 or from about 1:1 to about 1:0.1.

The process of the present invention is designed to minimize the contact time between mixing the aqueous solution of the aluminum hydroxyhalide salt having the Band III polymer concentration of at least about 20% with an aqueous solution of monomeric aluminum salt prior to drying. Minimizing the contact time helps to maintain the monomeric state and acidity of the monomeric aluminum salt. Long contact times may allow the monomeric aluminum salt to be neutralized by the aluminum hydroxyhalide salt resulting in the formation of aluminum dimmers, trimers and polymers. The contact time will vary according to process conditions, particularly temperature. High process temperatures, i.e. greater than 95° C., will require shorter contact times in order to prevent neutralization. For example, the contact time of the present invention may be from about 1 second to about 30 minutes, from about 1 second to about 5 minutes, or from about 1 second to about 1 minute. One non-limiting example of this process whereby such contact time can be achieved is by providing a flowing stream of the aqueous solution of an aluminum hydroxyhalide salt having a Band III polymer concentration of at least about 20% and providing a flowing stream of an aqueous solution of a monomeric aluminum salt, mixing the two streams via a static mixer, and directly flowing the resulting mixture into a spray drier wherein the resulting product may be rapidly dried to a powder.

The step of rapidly drying the mixture into a powdered product in the present invention can be achieved by any drying method known in the art provided that it rapidly converts liquid mixture to a powder. For example, drying time may be from about 1 second to about 30 minutes, from about 1 second to about 5 minutes, from about 1 second to about 2 minutes, or from about 1 second to about 1 minute. Spray drying may be used as the method of drying, however, any other method including, but not limited to, tray drying, freeze drying or vacuum drying can also be used.

The powder resulting from the process herein can be in the form of a particulate or other solid form. For example, powders may be in the form of flowable particulates. The average particle size of the particulates of the present invention may be, for example, less than about 75 microns, less than about 10 microns or less than about 5 microns but no less than about 0.1 microns. The average particle size can be controlled by any known effective particle size reduction method. Nonlimiting examples of suitable particle size reduction methods include grinding or the application of other suitable shear force to the preferred aluminum-only salt particulates.

The process of the present invention may also include the addition of other optional components such as a buffering material. For example, a water soluble amino acid buffer may be used. This buffering material can be added to either the aqueous solution of aluminum hydroxyhalide salts with a Band III polymer concentration of more than about 20% or the aqueous solution of monomeric aluminum salt. Adding the buffer to the aqueous solution of monomeric aluminum salt may be used provided a high level of monomeric aluminum is maintained in the final active. Suitable buffers include, but are not limited to, urea, neutral amino and salts of neutral amino acids, examples of which include glycine (including alkaline and alkaline earth glycinates and magnesium hydroxy glycinates), DL-valine, DL-alanine, arginine, L-proline, and combinations thereof. Further, for example, glycine, calcium glycinate or strontium glycinate may be used.

Active

The present invention provides an enhanced efficacy antiperspirant active using an improved aluminum-only salt. Aluminum-only salts of the present invention may have an aluminum to anion ratio of, for example, about 1.1:1 to about 1.8:1, about 1.2 to about 1.6 or from about 1.4 to about 1.6. Such ratios are capable of providing the desired efficacy benefit while preventing manufacturing equipment corrosion that could occur at lower ratios. The aluminum-only salts of the present invention also have a polymer size distribution that includes at least about 20% Band III polymers. The aluminum-only salts of the present invention may also have, for example, a Band III polymer concentration of at least about 25% or at least about 30% when analyzed by the size exclusion chromatography method as described hereinafter using Gel Permeation Chromatography (GPC). The aluminum-only salts of the present invention also have a level of monomeric aluminum ranging, for example, at least from about 2%, at least from about 3%, or at least about 4% and no more than from about 20%, no more than from about 15% or no more than from about 12% of the total aluminum.

Gel Permeation Chromotography (GPC)

Aluminum-only salts of the present invention are dissolved in 0.01M nitric acid and chromatographed using 5 μl injections in a series of three consecutive Waters μ Porasil Columns, 3.9×300 mm, 10 μm packing. The mobile phase is a 0.01M nitric acid solution prepared by diluting 1.76 ml of 69-71% nitric acid to a volume of 2.0 L using deionized water. The flow rate is 0.8 ml min$^{-1}$ through the columns. The chromatographic system used is from Hewlett Packard and includes an 1100 series isocratic pump, autosampler, and an HP1047A refractive index detector (equivalent instrumentation can be used).

Samples are prepared by diluting 1 part of the powdered active to 100 parts total solution by weight with the 0.01M HNO$_3$ solution. This is done immediately prior to analysis to prevent degradation. Aqueous solutions of the aluminum hydroxyhalide salts used in the present invention may be diluted at 2 to 10 parts of aluminum hydroxyhalide salts to 100 parts total water depending upon concentration of the aluminum hydroxyhalide salts to provide a similar concentration to the powder samples.

Relative peak areas and area ratios are calculated using a Waters Millennium Data System (Version 2.10 or equivalent). The peaks observed in the chromatogram are designated in order of appearance on the chromatogram as Bands I, II, III and IV (see FIG. 1). The concentration of Band III polymers is determined by dividing the peak area of Band III by the sum of the peak area for Bands I, II, III, and IV.

Nuclear Magnetic Resonance (NMR) of Monomeric Aluminum

The aluminum-only salts of the present invention also have a level of monomeric aluminum ranging, for example, at least from about 2%, at least from about 3%, or at least about 4% and no more than from about 20%, no more than from about 15% or no more than from about 12% of the total aluminum. The concentration of monomeric aluminum level can be determined using the following method:

A set of AlCl$_3$ standards for 0 to about 2.5% aluminum chloride can be prepared by dissolving AlCl$_3$.6H$_2$O (JT Baker 0498-01 98.9% purity) in D$_2$O. The aluminum content in each (or in the original standard) can be determined by EDTA/Zn$^{2+}$ back titrations as described in the US Pharmacopeia 24.

NMR analysis of each standard can be performed using a Bruker Avance 400 MHz instrument (or equivalent) under quantitative conditions in which 32 scans can be signal averaged. Aluminum chloride can be used as the chemical shift reference material and assigned to 0.0 ppm. Resonance areas (at 0.0 ppm) for the standards are measured using the Avance X-win NMR v3.5 software package (or equivalent). A calibration plot of resonance area versus aluminum concentration (Al ppm) is then created. The slope (m) and intercept (b) of the calibration plot can then be determined using a linear least squares fit.

Samples of the aluminum-only salts of the present invention can be prepared by weighing out 10 parts of active ingredient and diluted to a total solution weight of 100 parts with D$_2$O (Cambridge Isotope Labs DLM-4-100) with both sample weight and total solution weight being recorded. Solutions can be capped, shaken to solubilize and transferred into standard NMR tubes. Solutions can be analyzed using the same NMR method as the standard within 2 minutes of being prepared. The resonance area at 0.0 ppm of the sample can be determined and used to calculate the % monomeric aluminum via the following equation.

$$\% \text{ Monomeric Aluminum} = \frac{(\text{sample area} - \text{Intercept})}{\text{Slope}} \times \frac{(0.0001)}{(\text{sample weight} \times \% \text{ Al in sample})}$$

To use this equation, the percent aluminum in the sample must be determined. This may be accomplished using the EDTA/Zn$^{2+}$ back titrations as described in the US Pharmacopeia 24.

Antiperspirant Compositions

The antiperspirant compositions of the present invention comprise the antiperspirant active made in accordance with the composition and process of the current invention. The concentration of the active in such compositions should be sufficient to provide the desired antiperspirant and/or deodorant efficacy. For example, the concentration of the active may be at least from about 0.1%, at least from about 0.5% or at least from about 5% and no more than from about 60%, no more than from about 30% or no more than from about 26%, by weight of the composition.

The antiperspirant compositions of the present invention may be anhydrous. As used herein, the term "anhydrous" means that the composition contains, for example, less than about 5%, less than about 2%, less than about 0.1%, or zero percent, by weight, of water other than water of hydration bound to the antiperspirant active or other material in the composition.

The antiperspirant compositions of the present invention may further comprise any additional skin active ingredients or material known or otherwise suitable for use in topical antiperspirant and deodorant compositions. Nonlimiting examples include solid or liquid carriers, surfactants or other wash-off aids, deodorant actives (e.g., antimicrobials, adsorbents, deodorant perfumes), fragrances, chelating agents, residue masking agents, other skin active agents, moisturizers or emollients, inert solids such as talc or solid polyethylene, preservatives, processing aids, dyes or other colorants, or suspending agents.

The antiperspirant compositions of the present invention may be formulated into any solid, semi-solid or liquid product form suitable for topical application to the underarm or other area of the skin where application is desired. Nonlimiting examples of suitable product forms include gel or wax sticks, soft solids or creams, roll-ons, and aerosol or pump sprays.

Nonlimiting examples of suitable optional materials and product forms are described in U.S. Pat. No. 5,156,834 (Beckmeyer et al.); U.S. Pat. No. 5,718,890 (Putman et al.); U.S. Pat. No. 5,429,816 (Hofrichter et al.); U.S. Pat. No. 5,744,130 (Guskey et al.); U.S. Pat. No. 5,605,681 (Trandai et al.); U.S. Pat. No. 5,298,236 (Orr et al.); U.S. Pat. No. 4,985,238 (Tanner et al.); and U.S. Pat. No. 4,904,463 (Johnson et al.).

Method of Use

The antiperspirant compositions of the present invention, all of which contain the foregoing active, may be applied topically to the underarm or other area of the skin in an amount effective to treat or reduce perspiration wetness and/or malodor. For example, the composition may be applied in an amount ranging at least from about 0.1 gram and no more than from about 20 grams, no more than from about 10 grams, or no more than from about 1 gram, to the underarm or other desired area of the skin. The compositions are applied to the underarm or other area of the skin, one or two times daily, or twice daily, to achieve effective antiperspirant and/or malodor control over an extended period.

EXAMPLES

The following Examples can be made in accordance with the present invention.

Example 1

A commercial solution of 50% (41% anhydrous active) aluminum chlorohydrate (Summit Research Labs, Huegonot N.Y. ACH 303) can be diluted to 18% in water and heated for 180 minutes at 90° C. to create a Band III concentration greater than 20%. This temperature can be maintained during subsequent processing. Separately a 6.4% solution concentration of aluminum chloride in water can be created and held at room temperature. The two solutions can be pumped into a static mixer (SMX Static Mixer from Sulzer Company, inside diamter: 0.1875 inches, length: 2.57 inches) using a Sarah standard cassette pump (Manostat 72-500-000). The mixed solutions can be pumped directly from the static mixer to a Yamato Pulvis GA32r mini spray drier operated with an inlet temperature of 217° C., an outlet temperature of 99° C. and an airflow of 0.15 $m^3$/min. Flow rates can be 10.5 ml/min resulting in a solution contact time of approximately 1.13 min before drying. Specifications of the resulting powder are reported in table 1.

Comparative Example

A commercial solution of 50% (41% anhydrous active) aluminum chlorohydrate (Summit Research Labs, Huegonot N.Y. ACH 303) can be diluted to 18% in water and heated for 180 minutes at 90° C. to create a Band III concentration greater than 20%. This temperature can be maintained during subsequent processing. The solutions can be pumped directly from the static mixer to the previously described spray drier operated at the previously described conditions using the cassette pump. Specifications of the resulting powder are reported in table 1.

Example 2

A commercial solution of 50% (41% anhydrous active) aluminum chlorohydrate (Summit Research Labs, Huegonot N.Y. ACH 303) can be diluted to 18% in water and heated for 180 minutes at 90° C. to create a Band III concentration greater than 20%. This temperature can be maintained during subsequent processing. Separately a 3.1% solution of aluminum chloride in water can be created and held at room temperature. The two solutions can be pumped into the static mixer using the peristaltic pump. The mixed solutions can be pumped directly from the static mixer to the spray drier operated at the above conditions. Flow rates can be 10.5 ml/min resulting in a solution contact time of approximately 1.13 min before drying. Specifications of the resulting powder are reported in table 1.

Example 3

A commercial solution of 50% (41% anhydrous active) aluminum chlorohydrate (Summit Research Labs, Huegonot N.Y. ACH 303) is diluted to 18% in water and heated for 180 minutes at 90° C. to create a band III concentration greater than 20%. This temperature can be maintained during subsequent processing. Separately a 3.1% solution of aluminum chloride in water can be created and held at room temperature. Glycine can then be added to the aluminum chloride solution to create a 1% concentration and mixed completely. The two solutions can be pumped into the static mixer using the peristaltic pump. The mixed solutions can be pumped directly from the static mixer to the spray drier operated at the above conditions. Flow rates can be 10.5 ml/min resulting in a solution contact time of approximately 1.13 min before drying. Specifications of the resulting powder are reported in table 1.

TABLE 1

| | Example 1 | Comparative Example | Example 2 | Example 3 |
|---|---|---|---|---|
| Al:Cl Molar Ratio | 1.56* | 1.95 | 1.5 | 1.5 |
| Band III level | 29.2 | 38.9 | 33 | 32 |
| Percent Monomeric Aluminum | 3.4 | 0 | 9 | 6 |

*this value is higher than target of 1.25 due to chloride loss during spray drying.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for making an enhanced efficacy antiperspirant active, said method comprising the steps of:

(a) providing an aqueous solution of aluminum hydroxyhalide salt having a Band III polymer concentration of at least 20% based on a total polymer concentration of all Band I polymers, Band II polymers, Band III polymers, and Band IV polymers present in the aqueous solution, the aqueous solution having an aluminum to halide molar ratio greater than 1.5:1 and a total aluminum salt concentration of at least 10%;
(b) adding to the aqueous solution of step (a) an aqueous solution of a monomeric aluminum salt to form a mixture, the aqueous solution of monomeric aluminum salt having an aluminum to anion molar ratio of from about 0.1:1 to about 1:1; and
(c) drying the mixture to form a product as a powder with an average particle size of from about 0.1 microns to about 75 microns, the product having an aluminum to anion ratio of about 1.1:1 to about 1.8:1, a polymer size distribution including at least 20% Band III polymers, and a level of monomeric aluminum of from about 2% to about 20% based on the total weight of aluminum in the product, such that a contact time between the formation of the mixture in step (b) and the drying of the mixture in step (c) is from about 1 second to about 5 minutes;

wherein the monomeric aluminum salt is aluminum chloride.

2. The method of claim 1 wherein the aluminum hydroxyhalide salt is an aluminum chlorohydroxide selected from the group consisting of aluminum chlorohydrate and aluminum sesquichlorohydrate.

3. The method of claim 1 wherein the aqueous solution of monomeric aluminum salt posesses an aluminum to anion molar concentration of from about 0.3:1 to about 0.4:1.

4. The method of claim 2 wherein the aluminum chlorohydroxide possesses an aluminum to chloride molar ratio greater than 1.8:1.

5. The method of claim 1 wherein the contact time is from about 1 second to about 1 minute.

6. The method of claim 1 wherein the aqueous solution of a monomeric aluminum salt is at around room temperature when added to the solution of step (a).

7. A method for making an enhanced efficacy antiperspirant active, said method comprising the steps of:
(a) providing a first flowing stream of a first aqueous solution of an aluminum chlorohydroxide, the first aqueous solution having a total aluminum salt concentration of at least 10%, a metal to chloride molar ratio greater than 1.5:1, and a Band III polymer concentration of at least 20% based on a total concentration of all Band I polymers, Band II polymers, Band III polymers, and Band IV polymers present in the first aqueous solution;
(b) providing a second flowing stream of a second aqueous solution of aluminum chloride, the second aqueous solution having an aluminum to chloride molar ratio of from about 0.1:1 to about 1:1;
(c) coalescing the first flowing stream and the second flowing stream in a mixer to form a mixture, wherein the ratio of the first stream to the second stream is from about 1:1.5 to about 1:0.05;
(d) flowing the mixture directly from the mixer into a spray drier; and
(e) drying the mixture with the spray drier for a drying time of about 1 second to about 30 minutes to form the enhanced efficacy antiperspirant active as a powder with an average particle size of from about 0.1 microns to about 75 microns, the enhanced efficacy antiperspirant active having an aluminum to chloride ratio of about 1.1:1 to about 1.8:1, a polymer size distribution including at least 20% Band III polymers, and a level of monomeric aluminum of from about 2% to about 20% based on the total weight of aluminum in the enhanced efficacy antiperspirant active, such that a contact time between the formation of the mixture in step (c) and the drying of the mixture in step (e) is from about 1 second to about 5 minutes;

wherein the monomeric aluminum salt is aluminum chloride.

8. The method of claim 7 wherein the mixer is a static mixer.

9. The method of claim 7 wherein the contact time is from about 1 second to about 1 minute.

10. The method of claim 7, wherein the level of monomeric aluminum is from about 4% to about 20%, based on the total weight of aluminum in the enhanced efficacy antiperspirant active.

11. The method of claim 7 wherein the second aqueous solution has an aluminum to anion molar concentration of from about 0.3:1 to about 0.4:1.

* * * * *